(12) United States Patent
Hotier et al.

(10) Patent No.: US 7,582,206 B2
(45) Date of Patent: *Sep. 1, 2009

(54) PROCESS AND DEVICE FOR SIMULATED MOVING BED SEPARATION WITH A REDUCED NUMBER OF VALVES

(75) Inventors: Gerard Hotier, Rueil Malmaison (FR); Philibert Leflaive, Mions (FR); Sylvain Louret, Lyons (FR); Frederic Augier, Saint Symphorien D'Ozon (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 130 days.

This patent is subject to a terminal disclaimer.

(21) Appl. No.: 11/890,526

(22) Filed: Aug. 7, 2007

(65) Prior Publication Data

US 2008/0041788 A1 Feb. 21, 2008

(30) Foreign Application Priority Data

Aug. 8, 2006 (FR) .................................. 06 07272

(51) Int. Cl.
*B01D 15/08* (2006.01)
(52) U.S. Cl. .................................. 210/198.2; 210/659
(58) Field of Classification Search ................. 210/635, 210/656, 659, 662, 198.2
See application file for complete search history.

(56) References Cited

U.S. PATENT DOCUMENTS

| | | | |
|---|---|---|---|
| 4,434,051 A | | 2/1984 | Golem |
| 5,705,061 A * | | 1/1998 | Moran ..................... 210/198.2 |
| 5,882,523 A * | | 3/1999 | Hotier et al. ............... 210/659 |
| 5,972,224 A * | | 10/1999 | Hotier et al. ............... 210/659 |
| 6,017,448 A * | | 1/2000 | Hotier et al. ............. 210/198.2 |
| 6,093,317 A * | | 7/2000 | Capelle et al. ........... 210/198.2 |
| 6,146,537 A * | | 11/2000 | Ferschneider et al. ....... 210/659 |
| 6,156,197 A * | | 12/2000 | Dessapt et al. ........... 210/198.2 |
| 6,224,762 B1 * | | 5/2001 | Ferschneider et al. .... 210/198.2 |

(Continued)

FOREIGN PATENT DOCUMENTS

EP 0923970 A1 6/1999

(Continued)

*Primary Examiner*—Ernest G Therkorn
(74) *Attorney, Agent, or Firm*—Millen, White, Zelano & Branigan, P.C.

(57) ABSTRACT

A simulated moving bed (SMB) separation device comprising a column, beds Ai of adsorbent separated by plates Pi with a single distribution and extraction network for fluids, in particular feed F, desorbant D, raffinate R and extract B, and a plurality of two-way valves for distribution of said fluids, said valves being limited in number compared with the prior art. The column is divided into a plurality of sectors Sk with 2 or 3 superimposed plates, each sector Sk comprising an external bypass line Lk connected to each plate Pi of Sk via a connector comprising a plate valve Vi. Each line Lk comprises a controlled means for limiting its internal flow, and is connected to each of the fluid networks F, D, R, E via a single line comprising a single controlled two-way isolation valve to supply for sequential supply or withdrawal of the corresponding fluid F, D, R or E towards or from the sector Sk under consideration. The SMB device may be used for the separation of para-xylene or meta-xylene from an aromatic C8 cut.

11 Claims, 5 Drawing Sheets

U.S. PATENT DOCUMENTS

Figure 1:
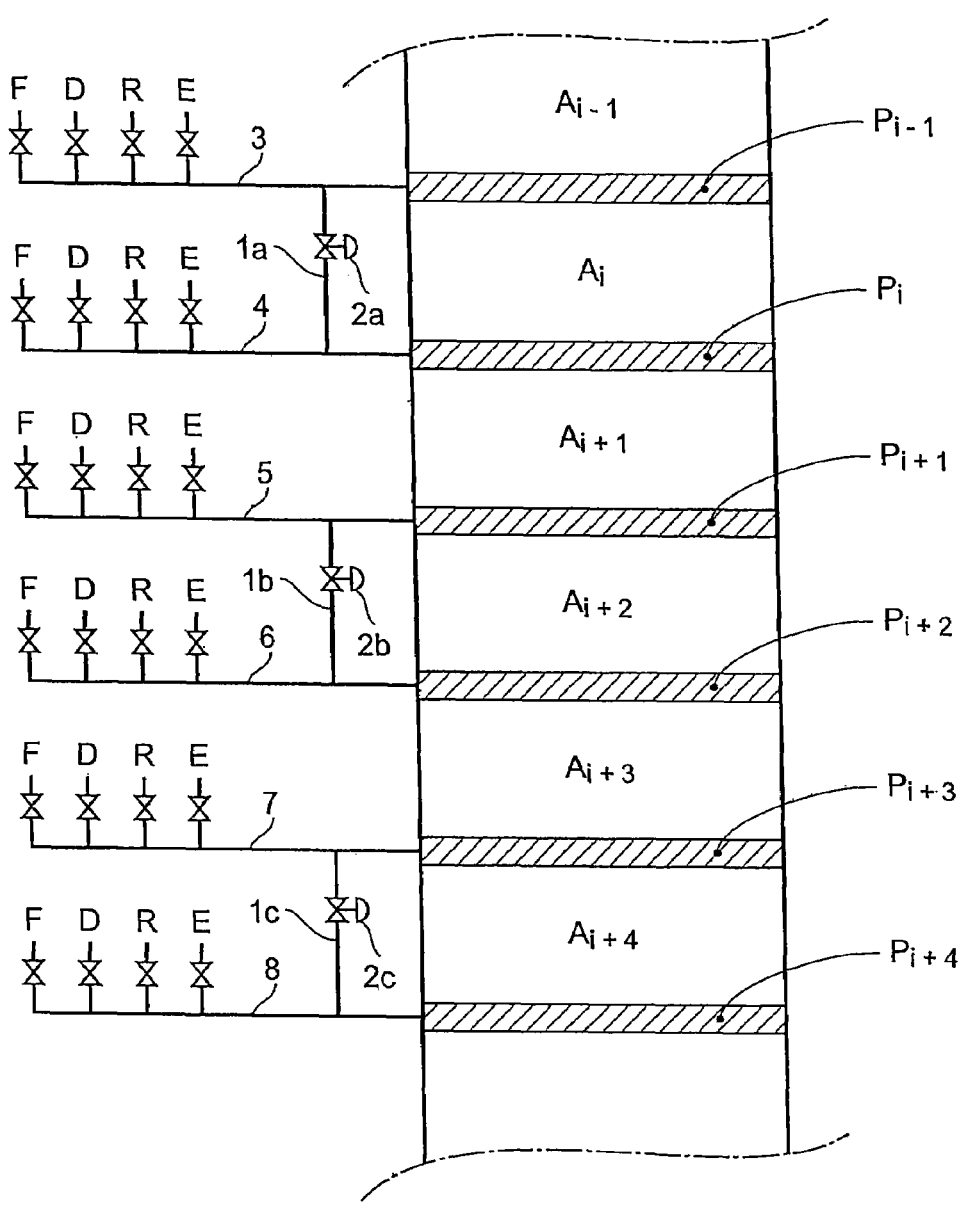

| | | | |
|---|---|---|---|
| 6,402,959 B1 * | 6/2002 | Dessapt et al. | 210/656 |
| 6,454,948 B2 * | 9/2002 | Ferschneider et al. | 210/659 |
| 6,537,451 B1 * | 3/2003 | Hotier | 210/198.2 |
| 6,797,175 B2 * | 9/2004 | Hotier | 210/659 |
| 7,288,200 B1 * | 10/2007 | Hotier et al. | 210/659 |
| 2001/0008220 A1 * | 7/2001 | Ferschneider et al. | 210/634 |
| 2003/0127394 A1 | 7/2003 | Hotier | |
| 2005/0269268 A1 * | 12/2005 | Hotier | 210/659 |
| 2006/0006113 A1 * | 1/2006 | Couenne et al. | 210/659 |
| 2008/0041788 A1 * | 2/2008 | Hotier et al. | 210/659 |
| 2008/0121586 A1 * | 5/2008 | Hotier et al. | 210/659 |
| 2008/0237132 A1 * | 10/2008 | Hotier et al. | 210/659 |

FOREIGN PATENT DOCUMENTS

| | | |
|---|---|---|
| EP | 1325772 A1 | 7/2003 |
| FR | 2782657 A1 | 3/2000 |
| FR | 2794663 A1 | 12/2000 |

* cited by examiner

PROCESS AND DEVICE FOR SIMULATED MOVING BED SEPARATION WITH A REDUCED NUMBER OF VALVES

FIELD OF THE INVENTION

The invention relates to the field of separation of natural or chemical products which are difficult to separate by distillation. A family of processes and associated devices are used which are known as "chromatographic" or "simulated moving bed" or "simulated counter-current" or "simulated co-current" separation devices which we shall hereinafter term "SMB".

A non-exclusive list of the fields concerned is:

separation of normal paraffins from branched paraffins, naphthenes and aromatics;

olefin/paraffin separation;

separation of para-xylene from other isomers in C8 aromatics;

separation of meta-xylene from other isomers in C8 aromatics;

separation of ethylbenzene from other isomers in C8 aromatics.

Beyond the refinery and petrochemicals plant, there are may other applications, including glucose/fructose separation, the separation of positional isomers of cresol, optical isomers, etc.

PRIOR ART

SMB chromatographic separation is well known in the art. In general, a simulated moving bed comprises at least three chromatographic zones, advantageously four or five, each of said zones being constituted by at least one bed or a portion of a column and included between two successive supply or withdrawal points. Typically, at least one feed F to be fractionated and a desorbant D (sometimes termed the eluent) are supplied and at least one raffinate R and extract E are withdrawn. The supply and withdrawal points are modified over time, typically shifted towards the bottom of a bed in a synchronous manner.

A plurality of advantageous variations can improve the function of that type of unit by making asynchronous permutations. Put simply, such asynchronous permutations act to compensate for the dead volume(s) of the recirculation pump(s), as indicated in U.S. Pat. No. 5,578,215, to work with a constant recycle rate on the recirculation pump to eliminate jerky flow rates and pressure, as indicated in U.S. Pat. No. 5,762,806, or finally to operate with at least two chromatographic zones each one of which is equivalent to a non integral number of adsorbent beds. This latter variation, as indicated in U.S. Pat. No. 6,136,198, U.S. Pat. No. 6,375,839, U.S. Pat. No. 6,712,973 and U.S. Pat. No. 6,413,419 is known as Varicol. Naturally, these three variations may be combined.

It should be noted that a multi-way rotary valve placing the incoming and outgoing fluids in communication with the beds disposed in the adsorption columns only allows a synchronous type permutation. For asynchronous permutations, a plurality of on-off valves is vital. This technical aspect is described below.

The prior art describes in detail various devices and processes which can carry out the separation of feeds in a simulated moving bed. Particular patents which may be cited are U.S. Pat. No. 2,985,589, U.S. Pat. No. 3,214,247, U.S. Pat. No. 3,268,605, U.S. Pat. No. 3,592,612, U.S. Pat. No. 4,614, 204, U.S. Pat. No. 4,378,292, U.S. Pat. No. 5,200,075 and U.S. Pat. No. 5,316,821. These patents also provide details of the function of a SMB.

SMB devices typically comprise at least one column (and frequently two), adsorbent beds $A_i$ disposed in that column, separated by plates $P_i$ with chamber(s) $C_i$ for distribution and/or extraction of fluids into or from the various beds of adsorbent, and controlled means for sequential distribution and extraction of fluids.

Each plate typically comprises a plurality of distributor-mixer-extractors or "DME" supplied via lines or "distribution/extraction manifolds". The plates may be of any type and any geometry, in particular with panels forming adjacent sectors in the column, for example panels with angular sectors such as those shown in FIG. 8 of U.S. Pat. No. 6,537,451, which are of symmetrical manifold supply, or parallel sectors such as cutouts in a circumference, as indicated in published patent application US-A-03/0,127,394, which are supplied bi-symmetrically. Preferably, the separation column comprises parallel sector type DME plates and bi-symmetrical supplies. Preferably again, the adsorbent is dense packed. This means that a larger quantity of adsorbent can be used in a given column and increases the purity of the desired product and/or the SMB flow rate.

Distribution over each bed requires flow from the preceding bed (principal circulating fluid along the principal axis of the column) to be collected, the possibility of injecting therein an auxiliary fluid or secondary fluid while mixing the two fluids to the best possible extent, or the possibility of removing part of the collected fluid, extracting it to send it out of the device and also to re-distribute a fluid onto the next bed.

To this end, it is possible to use in a plate $P_i$ chambers $C_{i,k}$ for distribution (injection/extraction) which may be separate or be common with the mixing chambers. Plates $P_i$ with one or more chambers are known, either supplied (or withdrawn) separately by different fluids at a given time, or supplied (or withdrawn) simultaneously and in parallel by the same fluid at a given time. In the first case, the plate is said to have a plurality of distribution networks and in the second case it has a single distribution network. The invention pertains exclusively to a device comprising plates with a single distribution network.

In general, either all of the fluid or principal flow is passed through the column in a manner described in U.S. Pat. No. 2,985,589, or a large part or all of that flow is evacuated as described in the process disclosed in U.S. Pat. No. 5,200,075.

A generic problem with all SMB devices is minimizing the pollution generated by the liquid in the various zones and volumes of the supply and withdrawal circuits for the fluids and plates during modifications to the supply and withdrawal points during operation of the SMB. When during the operating sequence a line, chamber or supply zone for a plate $P_i$ is no longer flushed by a process fluid, it becomes a dead zone in which the liquid stagnates, and only moves again when another process fluid moves in it. Since in SMB this is a different process fluid, the liquid in the dead zone is necessarily displaced by a liquid with a substantially different composition. Mixing or circulation over a short time interval of fluids with substantially different compositions thus introduces a deviation from the ideal operation, which proscribes discontinuities in composition.

A further problem may reside in any re-circulation between different zones of the same plate, which thus also induces a deviation from ideal operation.

To overcome these problems linked to re-circulation and dead zones, various techniques are already known in the prior art:

a) flushing of the lines and dead zones by a desorbant or relatively pure product has already been proposed. That technique prevents pollution of the desired product during its extraction. However, since the flushing liquid typically has a composition which is very different from the liquid it displaces, this introduces discontinuities in the composition which are prejudicial to ideal operation. This first flushing variation typically carries out "short duration flushes at a high concentration gradient". These flushes are brief to limit composition discontinuity effects.

b) As described in U.S. Pat. No. 5,972,224, another solution consists of passing the majority of the principal flow towards the interior of a column and a minority of that flow towards the exterior, typically 2% to 20% of the flow, via external bypass lines between neighbouring plates. This flush is typically carried out most of the time or continuously, so that the lines and zones are not "dead" but are flushed. Such a system with flushing via bypass lines is shown in FIG. 1 of U.S. Pat. No. 5,972,224 and repeated in a simplified version in FIG. 1 of the present application. Since the bypass lines are designed for a small flow, they may as a result be small in diameter, and comprise a small diameter valve, which reduces the cost of the system.

A first advantage of such a system is that the injection and withdrawal circuits for secondary fluids are flushed with liquid with a composition which is very close to the displaced liquid since firstly, the bypass derives from a neighbouring plate, and secondly, flushing is substantially continuous rather than discontinuous. Further, the flows in the bypasses are preferably determined so that the transit rate in each bypass is substantially the same as the rate of advance of the concentration gradient in the principal flow of the SMB. Hence, the various lines and capacities are flushed with a fluid which has a composition which is substantially identical to that of the liquid which is found therein and the liquid circulating in a bypass is re-introduced at a point where the composition of the principal flux is substantially identical. This second variation can thus carry out "long duration flushes with a small or zero concentration gradient".

A second advantage of this long duration flush system (outside the injection or withdrawal periods) is that it can remove the effects of possible re-circulation between zones of the same plate due to small pressure drop differences.

Regarding the function of a SMB, the controlled fluid distribution and extraction means of a SMB are typically one of the following two major types of technique:
either, for each plate, a plurality of on-off controlled valves for supplying or withdrawing fluids, said valves typically being located in the immediate vicinity of the corresponding plate, and in particular comprising, for each plate Pi, at least 4 controlled two-way on-off valves respectively to supply fluids F and D and withdraw fluids E and R;
or a multi-way rotary valve for supply or withdrawal of fluids over all of the plates.

The first technique uses two-way valves, which can be mass produced, resulting in increased reliability and a relatively low unit cost. The second technique uses only a single valve, but that single valve is a multi-way valve and necessarily is of special construction, of large dimensions and is extremely complex. Further, this second technology excludes the possibility of asynchronous permutations, as in the Varicol device.

The invention concerns SMB using conventional two-way valves, i.e. using the first of the two techniques described above. In particular, it concerns an improved device for simulated moving bed separation comprising a plurality of two-way on-off valves, but with a reduced number with respect to the prior art. It can be used both for SMB with synchronous permutations and for SMB with asynchronous permutations, for example a Varicol.

BRIEF DESCRIPTION OF THE INVENTION

The invention concerns an improved device for simulated moving bed separation belonging to the major simulated moving bed technique using a plurality of controlled two-way on-off valves, typically standard valves mass produced at low cost of the required high standard (seal/reliability).

One of the essential aims of the invention is to reduce the relative disadvantage of this type of SMB, which is to require a large number of controlled two-way valves. The invention can reduce the number of these valves, while retaining the advantage of being able to provide effective flushing of dead zones of the "long duration at a small or zero concentration gradient" type.

A further aim of the invention is to provide a device which requires a reduced number of two-way valves without the open/close frequency of those valves being increased with respect to the prior art; this along with the reduced number of valves limits the statistical risks of malfunction and thus increases the reliability of the system.

Finally, in a preferred variation of the device, the number of large diameter valves which allow circulation of the principal fluids of the SMB at their nominal flow rate can be further reduced.

The device of the invention may be used in new facilities, but is also compatible with various existing facilities on which it may be installed, by carrying out limited modifications. It is also compatible with various types and geometries of plates Pi, for example plates with angular sector panels or with parallel sectors, provided that said plates (or the majority thereof) are of the single distribution network type.

Thus, a means has been discovered which can substantially reduce the number of principal controlled valves, corresponding to the inlets/outlets for fluids for the SMB process: in the prior art, for each plate there is at least one set of 4 principal network valves for supply/withdrawal of F, D, R, E. This number is further increased if there are more than 4 fluids, for example if there are two raffinates R1, R2 or if a reflux RE is used which is rich in the desired product. In the prior art, the bypass lines, which have a small diameter, are only auxiliary lines which are not used by the fluids F, D, R, E (E1) (E2) (RE) at their nominal supply or withdrawal flow rate.

According to the invention, the column or the principal portion of that column is grouped into superimposed sectors Sk, each sector Sk comprising 2 or 3 adsorbant beds and 2 or 3 plates, and comprising a bypass line Lk. In contrast to the prior art, the fluids of the SMB use the line Lk at their nominal flow rate and a single set of principal network valves (supply or withdrawal) per column sector is used (rather than per plate as in the prior art), said valves being connected to the bypass line Lk to allow circulation of these fluids via Lk. According to the invention, "plate valves" are also provided, and means for limiting the flow rates of the bypass fluids, but the total number of valves remains substantially reduced, as will be explained below.

The invention also concerns a process for SMB separation using the device described above, in particular for the separation of para-xylene or meta-xylene from a feed of aromatic hydrocarbons containing 8 carbon atoms.

The invention also concerns the use of the device described above for separating an aromatic from an aromatics cut containing the same number of carbon atoms.

DETAILED DESCRIPTION OF THE INVENTION

Figure 2:
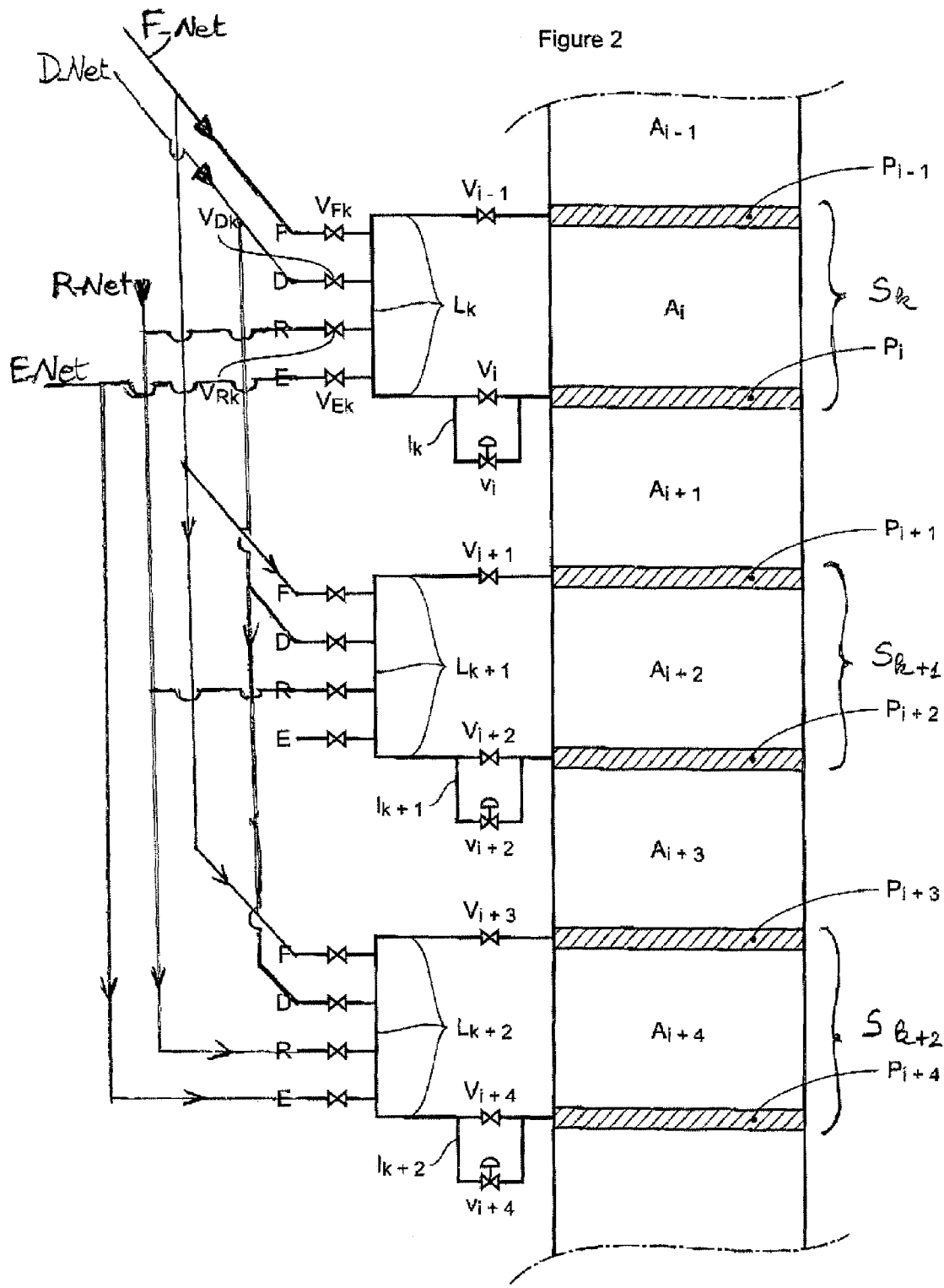
Figure 3:
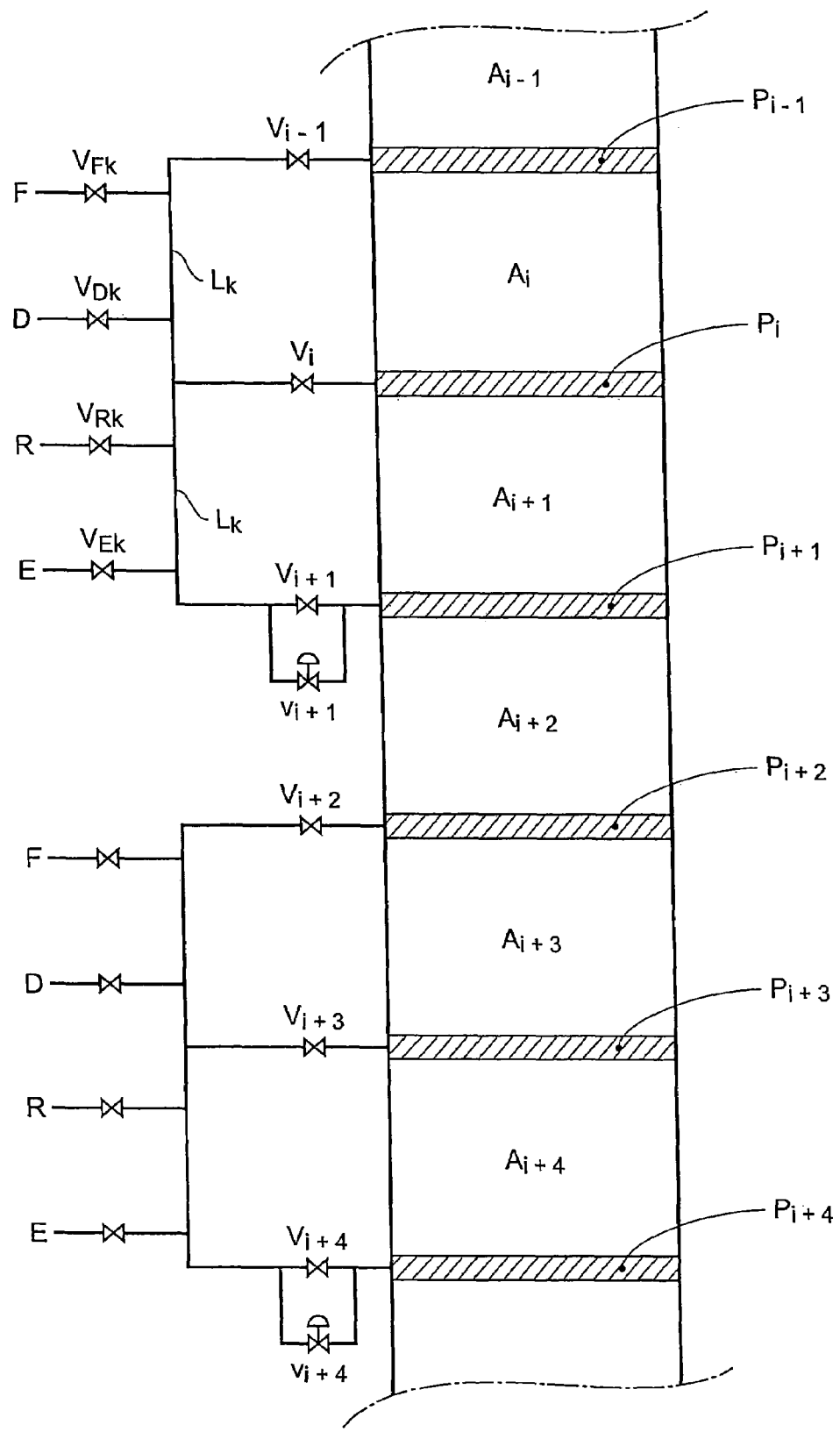

The invention will be better understood from the following description, made with reference to FIG. 1 (prior art) and FIGS. 2 and 3 (device of the invention).

To achieve one of the aforementioned aims, the invention thus proposes a device for separating at least one desired compound from a mixture comprising that compound by simulated moving bed adsorption comprising:

at least one column divided into a plurality of adsorbant beds Ai separated by distributor/extractor plates Pi to sequentially supply and extract at least two supply fluids: a feed F and a desorbant D, and at least two withdrawn fluids: a raffinate R and an extract E, Pi being disposed between the bed Ai and the immediately inferior bed Ai+1;

the device also comprising at least one feed network F-net, a desorbant network D-net, a raffinate network R-net and an extract network E-net, each of said networks being connected to the column via a plurality of intermediate lines comprising controlled two-way isolation valves termed network valves to sequentially supply or withdraw the fluids F, D, R, E;

in which the column is divided over at least the main portion of its height into a plurality of superimposed adjacent sectors Sk, each sector Sk being essentially constituted by a group of at least 2 and at most 5 successive beds of adsorbant and by the distributor/extractor plates Pi which are disposed immediately below said successive beds of adsorbant;

each of the distributor/extractor plates Pi of each of the sectors Sk uses a single common network for sequential supply and withdrawal of fluids F, D, R, E;

the plates Pi of each sector Sk are connected together via an external bypass line Lk connected to each plate Pi of Sk via a connector comprising a single controlled two-way isolation valve belonging to plate Pi, termed the plate valve Vi, to sequentially supply or withdraw fluids F, D, R, E to or from Pi;

each of said bypass lines Lk comprises at least one controlled means for limiting the flow circulating in Lk (such as a controlled valve+flow meter+valve programming system) which is either installed on line Lk or bypasses around a plate valve Vi or a plate Pi of Sk;

in which the bypass line Lk of each of the sectors Sk is connected to each of the F-net, D-net, R-net and E-net networks via a single line comprising a single network valve, respectively $V_{Fk}$, $V_{Dk}$, $V_{Rk}$, $V_{Ek}$, for sequential supply or withdrawal of fluid corresponding to F, D, R, E to or from the sector Sk under consideration;

and in which each plate Pi of the sector Sk is connected in a unique manner to each of the networks F-net, D-net, R-net and E-net via, in series, the connector comprising the plate valve Vi, then at least part of Lk, then said single line comprising said single network valve, respectively $V_{Fk}$, $V_{Dk}$, $V_{Rk}$, $V_{Ek}$.

Preferably, each sector Sk is essentially constituted by a group of 2 or 3 successive adsorbant beds. Variations of 4 or 5 successive beds result in columns with a higher total number of beds, to be able to produce different chromatographic zones.

In contrast to the prior art device, the device of the invention can use the bypass line Lk to circulate fluids F, D, R, E supplied to the SMB and withdrawn from the SMB at the sector Sk via a corresponding single set of network valves, instead of a set of network valves per plate Pi as in the prior art. This substantially reduces the overall number of controlled valves, even when the addition of supplemental valves, namely the plate valves Vi, is taken into account.

Said controlled valves: network valves and plate valves Vi, are typically high quality valves (reliability, seal, service life) carrying out the sequential operation of the SMB.

More generally, all of the controlled valves ensure the sequential function of the SMB: network valves, plate valves Vi, and also the valves of the controlled means for limiting the flow circulating in Lk must be considered, in accordance with the invention, as the "principal" valves of the SMB, connected to the column and controlled via the system for controlling the sequential function of the SMB (computer, programmable means or other equivalent system).

Certain principal valves for the sequential operation of the SMB were mentioned above as being unique to the invention: Vi for each plate Pi; a single set of network valves $V_{Fk}$, $V_{Dk}$, $V_{Rk}$, $V_{Ek}$ for each sector Sk. However, the scope of the invention encompasses the additional use of other valves such as occasional secondary isolation valves, typically with a far inferior quality, which may or may not be controlled, but not participating in the sequential operation of the simulated moving bed and, for example, being present for the purposes of dismantling any equipment: pump or principal valve used for sequential operation, etc.

Typically, the bypass line Lk, which is used to transmit all of the fluids F, D, R, E at their nominal flow rate, in the device of the invention, is no longer a small auxiliary line as in the prior art, but generally has an internal diameter which is at least equal to the largest diameter of the opening of the network valves connected to Lk to allow the fluids F, D, R, E to circulate without limiting capacity.

Because bypass lines Lk are used which can transport large flows, controlled flow rate limiter means are advantageously used to circulate a low flow as a bypass (typically 2% to 20% of the flow moving in the column). The term "bypass circulation" as used here means that a (small) fraction of the flow moving in the column is withdrawn from a plate and re-introduced into another plate of the same sector Sk. The term "controlled means" typically applies to a controlled valve, typically with a control system, starting from information provided by a flow meter. To this end, a flow rate regulating valve may be used which is installed directly on the line Lk. This valve is thus typically a gradual opening valve and not an on-off controlled valve (which has only 2 possible positions: fully open and closed).

However, in a preferred variation of the invention, at least one or preferably each of the bypass lines Lk comprises a controlled means for limiting the flow circulating in Lk, which is not installed directly on Lk but as a bypass around a plate valve Vi of a plate Pi of Sk, on a small secondary bypass $l_k$. This means is generally a controlled valve vi with a smaller diameter opening than that of Vi, for example with a diameter at most 60% or 50% that of Vi, for example in the range 10% to 50% of the diameter of Vi. When an internal flush is to be carried out as a bypass around Lk and this internal bypass flow is to be limited (circulating from one Sk plate to another Sk plate), plate valve Vi is closed and the small valve vi bypassing around Vi is opened. Thus, the use of a small secondary bypass $l_k$ around one of the plate valves Vi (typically the valve Vi of the lower plate Pi of Sk) allows a smaller opening diameter valve to be used than if the flow limiter means was a valve disposed on the principal bypass line Lk, which has a relatively larger diameter because Lk must allow circulation of fluids F, D, R, E at their nominal flow rate.

According to the invention, the connector comprising Vi must be interpreted as not including the small secondary bypass $I_k$ around Vi, nor the small valve vi disposed on $I_k$. This connector thus comprises a single valve Vi allowing circulation of the principal fluids F, D, R, E.

In a first variation, at least one sector Sk (and usually all of the sectors Sk) is constituted by two beds of adsorbant, Aj, Aj+1 and the two distributor/extractor plates Pj, Pj+1 which are respectively disposed immediately below said beds of adsorbant. The sectors are thus 2 beds and 2 plates Pi.

In a second variation, at least one sector Sk is constituted by three beds of adsorbant Aj, Aj+1, Aj+2 and the three distributor/extractor plates Pj, Pj+1, Pj+2 which are disposed immediately below the respective beds of adsorbant. The sectors are thus 3 beds and 3 plates Pi.

A sector Sk must be defined in the case of the column bottom. Typically, there is no plate Pn below an adsorbant bed An disposed at the column bottom as there is no need to distribute fluids into an immediately inferior bed. Further, in accordance with the invention, in this case it is assumed that the missing plate Pn is replaced by the lower outlet line from the column, typically connected either to the inlet to the same column, via a re-circulation pump, or to the head of a second separation column.

Preferably, the entire column (with the exception of the head plate, excluded by definition from the term "sector"), is constituted by superimposed adjacent sectors Sk.

All of the sectors Sk may thus be constituted by two adsorbant beds and the two distributor/extractor plates which are respectively disposed immediately below the adsorbant beds (or said lower outlet line assimilated with a lower plate). The column is thus substantially constituted by sectors with 2 beds and 2 plates. It may also be substantially constituted by sectors with 3 beds and 3 plates, or by an association of sectors with 2 beds and 2 plates and sectors with 3 beds and 3 plates. Finally, in a variation which is not preferred, it is also possible to include sectors Sk of the invention and one or more individual plates Pi supplied in accordance with the prior art, as shown in FIG. 1.

The invention described above in the case of 4 networks of fluids F, D, R, E may also be used in a similar manner when there are not 4 but 5 or 6 fluid networks, for example by using 2 raffinates R1, R2 and/or a reflux RE of product rich in the desired product. Thus, there are 5 or 6 network valves per sector Sk and line Lk.

The invention also concerns a separation process using the device described above, in which during a cycle each line Lk is used sequentially to circulate the fluids F, D, R, E at their nominal flow rate to or from each of the plates Pi of Sk via, in series, the plate valve Pi and one of the network valves $V_{Fk}$, $V_{Dk}$, $V_{Rk}$, $V_{Ek}$ and in which Lk is used by each of the fluids F, D, R, E over the whole of its length during one cycle.

In general, an internal flush of at least a portion of each of the bypass lines Lk is carried out when no network valve connected to Lk is open and all internal flushing of Lk is stopped when a network valve connected to Lk is open.

Preferably, an internal flush of Lk is carried out from plate Pi located in an upper position in Sk and towards the plate Pi+1 or Pi+2 which is located in a lower position in Sk, over all time periods when Sk is not connected to one of the fluid networks, and which is immediately before a period when one of the network valves connected to Sk is open to supply or withdraw one of the fluids to or from the plate Pi. This internal flush results in opening of Vi in the period preceding a supply or withdrawal period for a plate Pi (which also requires opening Vi) and avoids opening or closing Vi between these consecutive periods. The reduction in the number of movements of the valves reduces wear of said valves and increases the reliability of the device and the associated process.

In general, internal flushes are carried out of at least two and usually all the bypass lines Lk. Typically, the internal flush takes place over at least 20%, usually at least 40% or even at least 50% of the time.

The invention can carry out all sorts of chromatographic separations, in particular a process for separating para-xylene, as a product, from a feed of aromatic hydrocarbons containing 8 carbon atoms, or a process for separating metaxylene, as a product, from a feed of aromatic hydrocarbons containing 8 carbon atoms.

In general, it allows the device described above to be used to separate any aromatic hydrocarbon from a feed of aromatic hydrocarbons containing the same number of carbon atoms.

DESCRIPTION OF FIGURES AND OPERATION OF DEVICES SHOWN

Figure 4A:
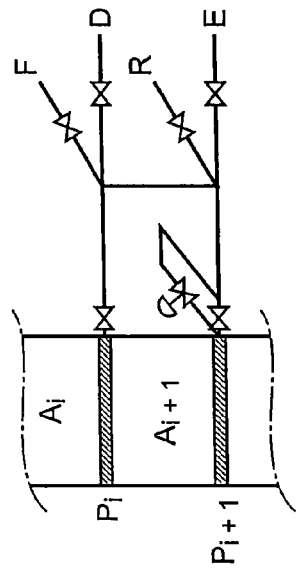
Figure 4B:
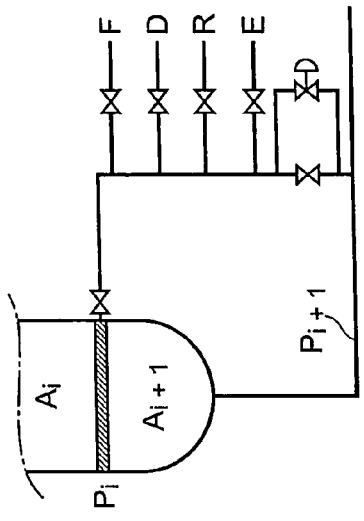
Figure 4C:
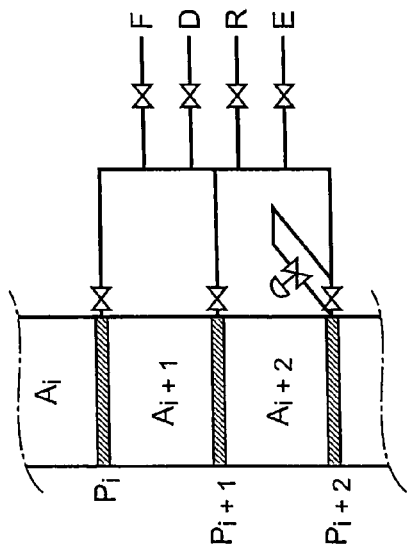
Figure 4D:
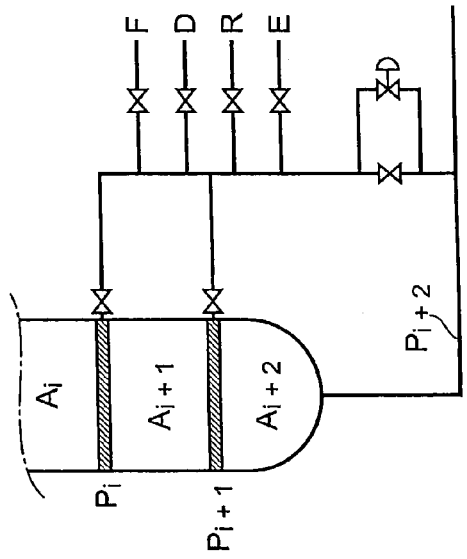
Figure 5A:
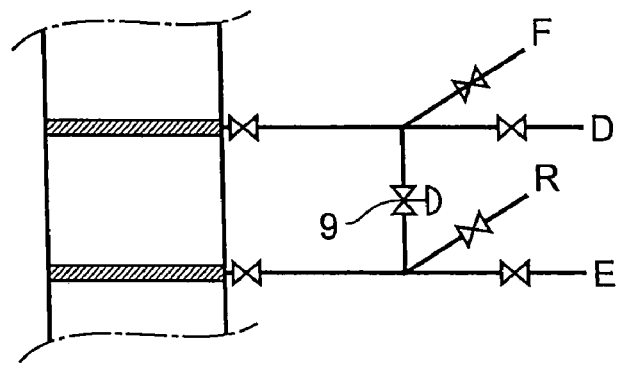
Figure 5B:
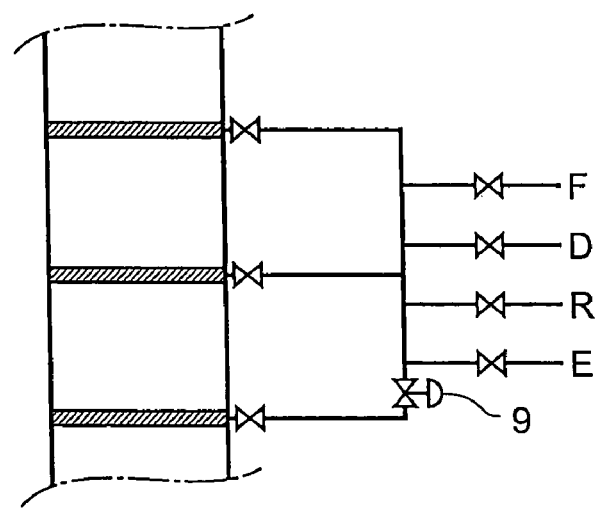

The invention will be readily understood from the accompanying drawings and description in which:

FIG. 1 is a diagrammatic representation of part of a prior art SMB device, with the corresponding network valves;

FIG. 2 diagrammatically shows part of a SMB device of the invention, comprising sectors Sk with 2 beds and 2 plates, with the corresponding network valves, plate valves and bypass flow rate limiting valves;

FIG. 3 diagrammatically shows part of a SMB device of the invention, comprising sectors Sk with 3 beds and 3 plates, with the corresponding network valves, plate valves and bypass flow rate limiter valves;

FIGS. 4a, 4b respectively diagrammatically show an intermediate sector and the bottom sector of the column in a device of the invention in the case in which sectors Sk has 2 beds and 2 plates;

FIGS. 4c, 4d respectively diagrammatically show an intermediate sector and the bottom sector of the column in a device of the invention in the case in which sectors Sk has 3 beds and 3 plates;

FIGS. 5a and 5b respectively diagrammatically represent an intermediate sector Sk with 2 beds and 2 plates and a sector Sk with 3 beds and 3 plates, in the case in which the flow rate limiting means for Lk is a regulating valve disposed on Lk.

We refer now to FIG. 1, representing part of a chromatographic column of a prior art SMB. Each of the beds of adsorbant Ai−1, Ai, Ai+1, Ai+2, Ai+3, Ai+4 is disposed above a plate Pi−1, Pi, Pi+1, Pi+2, Pi+3, Pi+4, and each of said plates is connected via a line, respectively 3, 4, 5, 6, 7, 8 to each of 4 fluid networks F, D, R, E via a valve (no reference). There are thus 4 principal valves per plate. Further, the plates are connected in pairs via a bypass line 1a, 1b, 1c comprising a small diameter valve, respectively 2a, 2b, 2c, to allow the passage of a limited bypass flow: 2% to 20% of the flow circulating in the column. In total, then, there are 4 principal valves and on average 0.5 small diameter valves (one for 2 plates) for each plate Pi, giving an average of 4.5 valves per plate.

The function of a SMB using such a column is well known to the skilled person. Typically, valve 2a, 2b or 2c of a bypass line is open when no fluid F, D, R, E is supplied or withdrawn from one of the 2 plates connected via the bypass line (bypass temporarily in service). In contrast, valve 2a, or 2b, or 2c of a bypass line is closed when one of fluids F, D, R, E is supplied or withdrawn to/from one of the 2 plates connected via the bypass line (bypass temporarily out of service).

FIG. 2 shows part of a column of a device of the invention comprising 3 sectors Sk, Sk+1, Sk+2, each comprising 2 beds of adsorbant and 2 plates located immediately below. The 2 plates of each sector are connected via a bypass line, respectively Lk, Lk+1, Lk+2 which is suitable for circulation of fluids F, D, R, E at their nominal flow rate. Each bypass line is connected to a set of 4 network valves for supply and withdrawal of fluids. In contrast to the prior art, this set of 4 valves supplies not 1 but 2 plates.

Thus, for the first sector Sk, there are 4 network valves $V_{Fk}$, $V_{Dk}$, $V_{Rk}$, $V_{Ek}$ supplying both Pi−1 and Pi.

Each plate is also connected to a corresponding bypass line Lk or Lk+1 or Lk+2 via a connector (corresponding to the horizontal part of the line in the Figure) comprising a single two-way controlled isolation valve belonging to the plate, termed a plate valve: Vi−1, Vi, Vi+1, Vi+2, Vi+3, Vi+4. Each lower plate valve of a sector: Vi, Vi+2, Vi+4 also has a small secondary bypass line Lk, Lk+1, Lk+2 provided with a valve which is typically of small diameter: vi, vi+2, vi+4.

In total, for each sector of 2 plates, there are 4 network valves, 2 plate valves and a small diameter valve in the secondary bypass, namely 7 valves, giving an average of 3.5 valves per plate.

The device operates as follows:

For the sector Sk, for example, when in a given period, one of the fluids F, D, R, E is to be supplied or withdrawn to/from the plate Pi−1, the corresponding network valve $V_{Fk}$, $V_{Dk}$, $V_{Rk}$, $V_{Ek}$ is opened as well as the plate valve Vi−1. The other network valves of the sector Sk are closed, as well as Vi and the small secondary bypass valve vi.

When in another period, one of the fluids F, D, R, E is to be supplied to or withdrawn from the plate Pi, the corresponding network valve $V_{Fk}$, $V_{Dk}$, $V_{Rk}$, $V_{Ek}$ and the plate valve Vi are opened. The other network valves of sector Sk are closed, as well as Vi−1. The small secondary bypass valve Vi may remain closed.

When in a third period fluids F, D, R, E are neither to be supplied to or withdrawn from plates Pi−1 and Pi, the network valves $V_{Fk}$, $V_{Dk}$, $V_{Rk}$, $V_{Ek}$ are closed. A limited bypass flow is then circulated in the line Lk (withdrawn from Pi−1 and injected into Pi), by opening Vi−1, closing Vi and opening the small secondary bypass valve vi. Thus, a small bypass flow is ensured via Lk. Vi is typically a regulating valve (with progressive opening) piloted by regulating the flow rate from a flow meter, not shown.

The other sectors si+1, Sk+2, function in an analogous manner.

FIG. 3 shows part of a column in a device of the invention comprising 2 sectors Sk, Sk+1, each comprising 3 beds of adsorbant and 3 plates located immediately below. The 3 plates of each sector are connected via a bypass line, respectively Lk, Lk+1 which can circulate fluids F, D, R, E at their nominal flow rate. Each bypass line is connected to a set of 4 network valves to supply and withdraw fluids. In contrast to the prior art, this set of 4 valves supplies not 1 but 3 plates.

Thus, for the first sector Sk, there are 4 network valves $V_{Fk}$, $V_{Dk}$, $V_{Rk}$, $V_{Ek}$ supplying Pi−1, Pi and Pi+1 at the same time.

Each plate is, as for the device of FIG. 2, connected to the corresponding bypass line via a connector comprising a plate valve. Each lower plate valve of a sector: Vi+1, Vi+4 also has a small secondary bypass line provided with a valve, typically of small diameter: vi+1, vi+4.

The device functions as follows:

For the upper sector, for example, when in a given period one of the fluids F, D, R, E is to be supplied to or withdrawn from plate Pi−1, the corresponding network valve $V_{Fk}$, $V_{Dk}$, $V_{Rk}$, $V_{Ek}$ is opened along with the plate valve Vi−1. The other network valves of sector Sk are then closed as well as Vi, Vi+1 and the small secondary bypass valve vi.

When in another period, one of the fluids F, D, R, E is to be supplied to or withdrawn from the plate Pi, the corresponding network valve $V_{Fk}$, $V_{Dk}$, $V_{Rk}$, $V_{Ek}$ and the plate valve Vi are opened. The other network valves of sector Sk are then closed along with Vi−1 and Vi+1. The small secondary bypass valve vi may remain closed.

When in a third period, one of fluids F, D, R, E is neither to be supplied to nor withdrawn from plates Pi−1 and Pi, network valves $V_{Fk}$, $V_{Dk}$, $V_{Rk}$, $V_{Ek}$ are closed. A limited bypass flow is then circulated in the line Lk. Two options are thus possible:

a small flow of may be withdrawn from Pi−1 and injected into Pi+1 by opening Vi−1, closing Vi and Vi+1 and opening the small secondary bypass valve vi+1;

it is also possible to withdraw a small flow of Pi and inject it into Pi+1, by opening Vi, closing Vi−1 and Vi+1 and opening the small secondary bypass valve vi+1.

Frequently, the plate (Pi−1, Pi) from which the bypass flow is withdrawn may be alternated to flush as many plates as possible.

Preferably, the last bypass flush period (before supplying or withdrawing a fluid F, D, R, E) is terminated by withdrawing via the upper plate Pi−1. In this case, valve Vi−1 is open during this period and there is no need for the valve to move at the start of the next period in which Pi−1 will be supplied or undergo withdrawal through Vi−1 since that valve is already open.

The other sectors Sk+1, Sk+2 function in an analogous manner.

One example of a type of function of a sector Sk with 3 beds of adsorbant and 3 plates (see FIG. 3) is as follows, in which the valves for the function of Sk which are open are mentioned and the valves which are not mentioned are closed:

Period 1: bypass flush from Pi−1 to Pi+1. Open valves: Vi−1, vi+1;

Period 2: injection of desorbant into Pi−1. Open valves: Vi−1, $V_{Dk}$;

Period 3: injection of desorbant into Pi. Open valves: Vi, $V_{Dk}$;

Period 4: injection of desorbant into Pi+1. Open valves: Vi+1, $V_{Dk}$;

Period 5: withdrawal of raffinate from Pi−1. Open valves: Vi−1, $V_{Rk}$;

Period 6: withdrawal of raffinate from Pi. Open valves: Vi, $V_{Rk}$;

Period 7: withdrawal of raffinate from Pi+1. Open valves: Vi+1, $V_{Rk}$;

Period 8: bypass flush from Pi to Pi+1. Open valves: Vi, vi+1;

Period 9: bypass flush from Pi−1 to Pi+1. Open valves: Vi, vi+1;

Period 10: bypass flush from Pi to Pi+1. Open valves: Vi, vi+1;

Period 11: bypass flush from Pi−1 to Pi+1. Open valves: Vi−1, vi+1;

Period 12: injection of feed into Pi−1. Open valves: Vi−1, $V_{Fk}$;

Period 13: injection of feed into Pi. Open valves: Vi, $V_{Fk}$;

Period 14: injection of feed into Pi+1. Open valves: Vi+1, $V_{Fk}$;

Period 15: bypass flush from Pi to Pi+1. Open valves: Vi, vi+1;

Period 16: bypass flush from Pi−1 to Pi+1. Open valves: Vi−1, vi+1;

Period 17: bypass flush from Pi to Pi+1. Open valves: Vi, vi+1;

Period 18: bypass flush from Pi−1 to Pi+1. Open valves: Vi−1, vi+1;

Period 19: bypass flush from Pi to Pi+1. Open valves: Vi, vi+1;

Period 20: bypass flush from Pi−1 to Pi+1. Open valves: Vi−1, vi+1;

Period 21: withdrawal of extract from Pi−1. Open valves: Vi−1, $V_{Rk}$;

Period 22: withdrawal of extract from Pi. Open valves: Vi, $V_{Rk}$;

Period 23: withdrawal of extract from Pi+1. Open valves: Vi+1, $V_{Rk}$;

Period 24: bypass flush from Pi to Pi+1. Open valves: Vi, vi+1.

The principles which allow the preferred sequencing to be established in the case of sectors with 3 beds of adsorbant and 3 plates are as follows:

1) each time one of the principal fluids (F, D, R, E) is withdrawn or injected using a network valve in a bypass line Lk, this network valve remains open three times in succession (during the successive 3 periods). The first time, the upper plate valve allows connection to the upper plate Pi−1, and the lower plate valves as well as the small bypass fluid control valve are closed. The second time, the intermediate plate valve allows connection to the intermediate plate Pi and the valves of the upper and lower bed as well as the small bypass fluid control valve are closed. The third time, the lower plate valve allows connection to the lower plate Pi+1 and the upper plate valves as well as the small fluid bypass control valve are closed.

2) Outside the periods for injection or withdrawal of the principal fluids (F, D, R, E), a bypass flow is circulated in Lk. The lower plate valve Vi+1 is closed and the small control valve vi+1 located in the secondary bypass around Vi+1 regulates the bypass flow via the secondary bypass, this flow alternately coming from the upper, Pi−1, and intermediate plates, Pi. During the last period during which a bypass fluid circulates in Lk prior to supply or withdrawal of one of the principal fluids, the valve of the upper plate Vi−1 (connected to plate Pi−1) is preferably opened and may then remain open during the next period.

FIGS. 4a and 4b diagrammatically represent a sector with 2 beds and 2 plates. FIG. 4b shows such a sector at the column bottom. According to the invention, it is assumed that the line referred to as Pi+1 by definition replaces the plate located below the bed Ai+1, this plate being absent from the column bottom.

In analogous manner, FIGS. 4c and 4d diagrammatically represent a sector with 3 beds and 3 plates. FIG. 4d shows such a sector at the column bottom. According to the invention, it is assumed that the line referred to as Pi+2 by definition replaces the plate located below the bed Ai+2, said plate being absent form the column bottom.

FIGS. 5a and 5b respectively represent a sector Sk with 2 beds and 2 plates, and a sector Sk with 3 beds and 3 plates in which the bypass flow limiting means does not include a secondary bypass with a valve vi but a valve with a larger diameter 9 disposed on the line Sk itself (with associated flow rate measurement means, not shown).

Best Implementation

The best implementation of the invention is a SMB wherein the column or columns are essentially constituted by sectors Sk with 3 beds and 3 plates. In such a device, by way of example 24 beds and 24 plates (for example 2 columns in a loop of 12 beds and 12 plates each), only 24 plate valves and 4×8=32 network valves are required (4 for each of the 8 sectors Sk which are required), i.e. 56 principal valves to which 8 small regulation valves must be added (secondary bypass), i.e. a total of 64 valves, which represents an average of 2.67 valves per plate.

In the prior art corresponding to FIG. 1, the equivalent SMB requires 4×24=96 principal valves (4 valves per plate) and 12 valves of reduced diameter, i.e. a total of 108 valves, i.e. 4.5 valves per plate.

The device of the invention as described may be used for any process for chromatographic separation, in particular to separate an aromatic hydrocarbon from a feed of aromatics essentially containing 8 carbon atoms and including that hydrocarbon.

In particular, it may be used to separate para-xylene from an aromatic cut essentially composed of c8 hydrocarbons, using toluene or para-diethylbenzene as a desorbant and a zeolite as an adsorbant as described, for example, in FR-A-2 789 914. It may also be used to separate meta-xylene from an aromatic c8 cut, using toluene or tetraline as a desorbant and an adsorbant such as that described in U.S. Pat. No. 5,900,523 and patent applications FR-A-05/52.485 and FR-A-05/52.486.

It may also be used to separate one or more normal paraffins (separated from the remainder of the hydrocarbons) from a mixture of hydrocarbons, in particular paraffinic or paraffinic and naphthenic, for example using normal butane or normal pentane as the desorbant (optionally isooctane as in inert diluent) and a 5A zeolite as the adsorbant.

Finally, it may be used to separate at least one olefin from a hydrocarbon cut comprising said hydrocarbon, under conditions known in the art, for example using an X zeolite exchanged with calcium.

The invention is not limited to the above description and to carry it out, the skilled person is at liberty to employ any other characteristic technique which is known in the art.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 06/07.272, filed Aug. 8, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device for separating at least one desired compound from a mixture comprising said compound, by simulated moving bed adsorption comprising:

at least one column divided into a plurality of adsorbant beds Ai separated by distributor/extractor plates Pi for sequential supply and extraction of at least two supply fluids: a feed F and a desorbant D, and at least two withdrawn fluids: a raffinate R and an extract E, Pi being disposed between the bed Ai and the immediately inferior bed Ai+1; the device also comprising networks of fluids, i.e. at least a feed network P-net, a desorbant network D-net, a raffinate network R-net and an extract network B-net, each of said networks being connected to the column via a plurality of lines comprising two-way controlled isolation valves termed network valves, for sequential supply or withdrawal of said fluids;

in which the column is divided, over at least the major portion of its height, into a plurality of superimposed adjacent sectors Sk, each sector sk essentially being constituted by a group of at least 2 and at most 5 successive beds of adsorbant and by distributor/extractor plates Pi which are disposed immediately below said successive beds of adsorbant;

each of the distributor/extractor plates Pi of each of the sectors Sk is a single common network for sequential supply and withdrawal of fluids F, D, R, E;

the plates Pi of each sector Sk are connected together via an external bypass line Lk connected to each plate Pi of Sk via a connector comprising a single two-way controlled isolation valve belonging to the plate Pi, termed the plate valve Vi, for sequential supply or withdrawal of fluids F, D, R, E into or from Pi;

each of said bypass lines Sk comprises at least one controlled means for limiting the flow rate in Lk, which is either installed on the line Lk or in a bypass around a plate valve Vi of a plate Pi of Sk;

in which the bypass line Lk of each of the sectors Sk is connected to each of the networks F-net, D-net, R-net and E-net via a single line comprising a single network valve, respectively $V_{Fk}$, $V_{Dk}$, $V_{Rk}$, $V_{Ek}$, for sequential supply or withdrawal of the corresponding fluid F, D, R, E to or from the sector Sk under consideration; and in which each plate Pi of the sector Sk is uniquely connected to each of the networks F-net, D-net, R-net and B-net via, in series, the connector comprising the plate valve Vi then at least a portion of Lk then said single line comprising said single network valve, respectively $V_{Pk}$, $V_{Dk}$, $V_{Rk}$, $V_{Ek}$.

2. A device according to claim 1, in which each sector Sk is essentially constituted by a group of 2 or 3 successive beds of adsorbant.

3. A device according to claim 1, in which the bypass line Lk has an internal diameter equal to at least the largest opening diameter of the network valves connected to Lk.

4. A device according to claim 1, in which at least one sector Sk is constituted by two beds of adsorbant Aj, Aj+1 and the two distributor/extractor plates Pj, Pj+1 which are respectively disposed immediately below the beds of adsorbant.

5. A device according to claim 4, in which all of the sectors Sk are constituted by two beds of adsorbant and the two distributor/extractor plates which are respectively disposed immediately below the beds of adsorbant or said assimilated lower outlet line.

6. A device according to claim 4, in which at least one sector Sk is constituted by three beds of adsorbant Aj, Aj+1, Aj+2 and the three distributor/extractor plates Pj, Pj+1, Pj+2 which are respectively disposed immediately below said beds of adsorbant.

7. A device according to claim 1, in which at least one sector Sk is constituted by three beds of adsorbant Aj, Aj+1, Aj+2 and the three distributor/extractor plates Pj, Pj+1, Pj+2 which are respectively disposed immediately below said beds of adsorbant.

8. A device according to claim 7 in which, for each sector Sk with three plates Pj, Pj+1, Pj+2, the bypass line Lk comprises a first means for limiting the flow between Pj and Pj+1 and a second means for limiting the flow between Pj+1 and Pj+2.

9. A device according to claim 1, in which the whole column is constituted by said adjacent superimposed sectors Sk, the column comprising a lower outlet line assimilated to a plate Pn corresponding to the lower bed of adsorbant An.

10. A device according to claim 1, in which each of said bypass lines Lk comprises at least one controlled means for limiting the flow circulating in Lk, which is installed as a bypass about a plate valve Vi of a plate Pi of Sk.

11. A device according to claim 10, in which said means for limiting the flow circulating in Lk installed as a bypass around said plate valve Vi comprises a controlled valve with a smaller diameter opening than that of Vi.

* * * * *

UNITED STATES PATENT AND TRADEMARK OFFICE
CERTIFICATE OF CORRECTION

| | | |
|---|---|---|
| PATENT NO. | : 7,582,206 B2 | Page 1 of 1 |
| APPLICATION NO. | : 11/890526 | |
| DATED | : September 1, 2009 | |
| INVENTOR(S) | : Hotier et al. | |

It is certified that error appears in the above-identified patent and that said Letters Patent is hereby corrected as shown below:

On the Cover, Section (57), line 4 reads "particular feed F, desorbant D, raffinate R and extract B, and" should read --particular feed F, desorbant D, raffinate R and extract E, and--.

Column 13, line 12 reads "fluids, i.e. at least a feed network P-net, a desorbant", should read --fluids, i.e. at least a feed network E-net, a desorbant--.

Column 13, line 14 reads "network B-net, each of said networks being connected to", should read --network E-net, each of said networks being connected to--.

Column 13, line 46 reads "B-net via, in series, the connector comprising the plate", should read --E-net via, in series, the connector comprising the plate--.

Signed and Sealed this

Thirteenth Day of October, 2009

David J. Kappos
*Director of the United States Patent and Trademark Office*